US011133101B2

(12) United States Patent
Srivastava et al.

(10) Patent No.: US 11,133,101 B2
(45) Date of Patent: Sep. 28, 2021

(54) METHOD AND SYSTEM FOR DATA DRIVEN COGNITIVE CLINICAL TRIAL FEASIBILITY PROGRAM

(71) Applicant: Tata Consultancy Services Limited, Mumbai (IN)

(72) Inventors: Anupam Srivastava, Noida (IN); Devraj Goulikar, Mumbai (IN); Sanjaykumar Madhukar Patil, Mumbai (IN); Vishal Ramanlal Jain, Mumbai (IN); Saurabh Das, Mumbai (IN); Ashish Omprakash Indani, Mumbai (IN); Niraj Vyas, Thane (IN); Charusheela Shashikant Thakur, Mumbai (IN)

(73) Assignee: Tata Consultancy Services Limited, Mumbai (IN)

( * ) Notice: Subject to any disclaimer, the term of this patent is extended or adjusted under 35 U.S.C. 154(b) by 160 days.

(21) Appl. No.: 16/421,279

(22) Filed: May 23, 2019

(65) Prior Publication Data

US 2019/0362838 A1  Nov. 28, 2019

(30) Foreign Application Priority Data

May 23, 2018 (IN) .............................. 201821019402

(51) Int. Cl.
*G16H 40/20* (2018.01)
*G16H 10/20* (2018.01)
(Continued)

(52) U.S. Cl.
CPC .............. *G16H 40/20* (2018.01); *G06N 3/08* (2013.01); *G06Q 10/06393* (2013.01); *G16H 10/20* (2018.01)

(58) Field of Classification Search
CPC ........ G16H 10/20; G16H 10/60; G16H 50/70; G16H 70/40; G16H 40/20; G16H 50/50;
(Continued)

(56) References Cited

U.S. PATENT DOCUMENTS 8,706,537 B1 * 4/2014 Young .................... G06Q 10/10
                                                     705/7.11
9,467,450 B2   10/2016 Paffel et al.
(Continued)

FOREIGN PATENT DOCUMENTS

WO    WO-2014/033747       3/2014

OTHER PUBLICATIONS

Abstracts from the society for clinical trials annual meeting, boston, massachusetts, USA—May 19-22, 2013. (2013). Clinical Trials, 10(2), n/a-S88.doi:http://dx.doi.org/10.1177/1740774513497438, A07, "Identifying Atypical Sites with Central Statisical Monitoring", Doffagne, Erik, (Year: 2013).*

(Continued)

*Primary Examiner* — Joseph D Burgess
(74) *Attorney, Agent, or Firm* — Finnegan, Henderson, Farabow, Garrett & Dunner LLP

(57) ABSTRACT

This disclosure relates generally to clinical trial management, and more particularly to method of performing a data driven cognitive clinical trial feasibility analysis. In one embodiment, the method comprising (a) receiving, a plurality of protocol requirements to initiate a clinical trial site feasibility; (b) identifying, a plurality of meta-data for at least one protocol requirement from the plurality of protocol requirements; (c) obtaining, an exhaustive list of historic clinical trial site data for the identified meta-data from a site data repository; (d) obtaining, an exhaustive list of third party clinical trial site data for identified meta-data from a third party data repository; and (e) assessing, the exhaustive (Continued)

list of clinical trial site data and the exhaustive list of third party clinical trial site data to obtain a list of identified clinical trial site feasibility.

10 Claims, 9 Drawing Sheets

(51) Int. Cl.
*G06N 3/08* (2006.01)
*G06Q 10/06* (2012.01)

(58) Field of Classification Search
CPC ........ G16H 10/40; G16H 15/00; G16H 10/00; G06Q 10/06393; G06Q 10/00; G06Q 50/24; G06Q 10/06395; G06Q 10/0639; G06N 20/00; G06N 3/0454; G06N 3/02
See application file for complete search history.

(56) References Cited

U.S. PATENT DOCUMENTS

| | | | | |
|---|---|---|---|---|
| 2010/0088245 | A1* | 4/2010 | Harrison | G16H 40/20 705/317 |
| 2013/0304504 | A1* | 11/2013 | Powell | G16H 20/90 705/3 |
| 2013/0311196 | A1* | 11/2013 | Fay | G06Q 10/0635 705/2 |
| 2014/0222444 | A1 | 8/2014 | Cerello et al. | |
| 2016/0147953 | A1* | 5/2016 | Menon | G16H 10/20 705/3 |
| 2016/0180245 | A1* | 6/2016 | Tereshkov | G06F 16/2237 706/12 |
| 2016/0300040 | A1* | 10/2016 | Dietlin | G06F 16/29 |
| 2018/0046780 | A1* | 2/2018 | Graiver | G06F 40/205 |
| 2019/0131016 | A1* | 5/2019 | Cohen | G16H 70/60 |
| 2019/0304575 | A1* | 10/2019 | Beltre | G06N 5/022 |

OTHER PUBLICATIONS

Yang E, O'Donovan C, Phillips J, Atkinson L, Ghosh K, Agrafiotis DK. Quantifying and visualizing site performance in clinical trials. Contemp Clin Trials Commun. 2018;9:108-114. Published Jan. 31, 2018. doi:10.1016/j.conctc.2018.01.005 (Year: 2018).*

* cited by examiner

| Vendor request | | | | | | | |
|---|---|---|---|---|---|---|---|
| Show 10 Entries | | | Search: | | Print | PDF | Excel |
| Request ID | Vendor name | Activity description | Request date | Planned received date | Actual received date | Status | TAT (In days) |
| 010001 | IMS | Site list for India | 2017-11-02 | 2018-03-01 | | ○ | |
| 110001 | KBO China | Site list for China | 2017-02-06 | 2018-03-01 | | ● | |

Showing 1 to 2 of 2 entries                    Previous  1  Next

Create request

METHOD AND SYSTEM FOR DATA DRIVEN COGNITIVE CLINICAL TRIAL FEASIBILITY PROGRAM

PRIORITY CLAIM

This U.S. patent application claims priority under 35 U.S.C. § 119 to: India Application No. 201821019402, filed on May 23, 2018. The entire contents of the aforementioned application are incorporated herein by reference.

TECHNICAL FIELD

This disclosure relates generally to clinical trial management, and more particularly to method and system for performing a data driven cognitive clinical trial feasibility analysis.

BACKGROUND

Clinical trials are research experiments performed on animals/humans to test new treatments, interventions or tests to prevent, detect, treat or manage various diseases or medical conditions. The clinical trials are one of the final stages of Research and Development (R & D) process that mostly begins in a laboratory and concludes in a clinical trial site, where tests are conducted on humans/animals. The R & D process follow strict, scientific standards which protect patients and help produce reliable clinical trial results. Further, to produce reliable clinical trial results, clinical trial site feasibility is a highly critical factor. Efficient and relevant clinical trial site feasibility not only helps to establish credibility and/or acceptability of new treatments, interventions or tests to prevent, detect, treat or manage various diseases or medical conditions but also to cut down on financial and monitoring resources required by a clinical trial. Further requirement protocol is applied to clinical trial site feasibility, however relative importance of each protocol may vary according to type/phase of trial, trial objective(s), available funds/resources, and so on while also considering political/economic and regulatory climate/stability as these can vastly affect a clinical trial site's ability to deliver over the course of a clinical trial.

Existing techniques for the clinical trial site feasibility are mostly manual with high dependency on investigators, which may result in lack of complete information due to reasons like limited experience, estimation of rough estimates or underestimation of site details and so on. The clinical trials are conducted on humans or patients with diverse background and it is a very tedious task to monitor and retain the diverse patient community for an entire period of clinical trial program as clinical trial sites are spread across the globe, wherein communication with each individual patient regarding their visit schedules, drug updates, drug delivery schedules, missing appointments are often miscommunicated or missed out. Another challenge is to authenticate the patient and ensure patients are not fraudulent. Furthermore, an exhaustive historic data and corresponding analytics is available for clinical trial site feasibility, however site selection criteria is generally not well defined, which makes clinical trial site feasibility from the existing resources a big challenge.

SUMMARY

Embodiments of the present disclosure present technological improvements as solutions to one or more of the above-mentioned technical problems recognized by the inventors in conventional systems. For example, in one embodiment, a method for performing a data driven cognitive clinical trial feasibility analysis is provided. The method comprises (a) receiving, via one or more hardware processors, a plurality of protocol requirements to initiate a clinical trial site feasibility; (b) identifying, via the one or more hardware processors, a plurality of meta-data for at least one protocol requirement from the plurality of protocol requirements; (c) obtaining, via the one or more hardware processors, an exhaustive list of historic clinical trial site data for the identified meta-data from a site data repository; (d) obtaining, via the one or more hardware processors, an exhaustive list of third party clinical trial site data for identified meta-data from a third party data repository; and (e) assessing, via the one or more hardware processors, the exhaustive list of clinical trial site data and the exhaustive list of third party clinical trial site data to obtain a list of identified clinical trial site feasibility.

In an embodiment, the plurality of protocol requirements may be structured/unstructured. In an embodiment, the meta-data may include at least one critical and relevant question identified from the received protocol requirement. In an embodiment, the meta-data may be identified based on an exhaustive list of historic meta-data present in a meta-data repository. In an embodiment, the site data repository may include data associated with at least one of (i) an exhaustive repository of historical site demographic and operational Information, (ii) a standard Key Performance Indicator (KPI), and (iii) key risk indicator (KRI). In an embodiment, the method further include analyzing, via the one or more hardware processors, an adequate exhaustive list of clinical trial site data. In an embodiment, the method further include at least one of: (a) determining, by via the one or more hardware processors, at least one of: (i) clinical trial site's overall performance basis, and (ii) overall site score among initial sites from the exhaustive list of clinical trial sites by performing a trending analysis at a KPI/KRIs level across time points; and (b) estimating, a Red, Amber, and Green (RAG) score based on the overall site score. In an embodiment, the method further include analyzing, by via the one or more hardware processors, an inadequate exhaustive list of clinical trial site data to obtain initial clinical trial site feasibility.

In another embodiment, a processor implemented system to perform a data driven cognitive clinical trial feasibility analysis is provided. The system includes a memory storing instructions; one or more communication interfaces; and one or more hardware processors coupled to the memory via the one or more communication interfaces, wherein the one or more hardware processors are configured by the instructions to: (a) receive, a plurality of protocol requirements to initiate a clinical trial site feasibility; (b) identify, a plurality of meta-data for at least one protocol requirement from the plurality of protocol requirements; (c) obtain, an exhaustive list of historic clinical trial site data for the identified meta-data from a site data repository; (d) obtain, an exhaustive list of third party clinical trial site data for identified meta-data from a third party data repository; and (e) assess, the exhaustive list of clinical trial site data and the exhaustive list of third party clinical trial site data to obtain a list of identified clinical trial site feasibility.

In an embodiment, the plurality of protocol requirements may be structured/unstructured. In an embodiment, the meta-data may include at least one critical and relevant question identified from the received protocol requirement. In an embodiment, the meta-data may be identified based on an exhaustive list of historic meta-data present in a meta-data repository. In an embodiment, the site data repository may include data associated with at least one of (i) an exhaustive repository of historical site demographic and operational Information, (ii) a standard Key Performance Indicator (KPI), and (iii) key risk indicator (KRI). In an embodiment, the one or more hardware processors may be further configured to analyze, an adequate exhaustive list of clinical trial site data. In an embodiment, the one or more hardware processors may be further configured to at least one of: (a) determine, by via the one or more hardware processors, at least one of: (i) clinical trial site's overall performance basis, and (ii) overall site score among initial sites from the exhaustive list of clinical trial sites by performing a trending analysis at a KPI/KRIs level across time points; and (b) estimate, a Red, Amber, and Green (RAG) score based on the overall site score. In an embodiment, the one or more hardware processors may be further configured to analyze, an inadequate exhaustive list of clinical trial site data to obtain initial clinical trial site feasibility.

In yet another embodiment, there are provided one or more non-transitory machine readable information storage mediums comprising one or more instructions which when executed by one or more hardware processors causes (a) receiving, via one or more hardware processors, a plurality of protocol requirements to initiate a clinical trial site feasibility; (b) identifying, via the one or more hardware processors, a plurality of meta-data for at least one protocol requirement from the plurality of protocol requirements; (c) obtaining, via the one or more hardware processors, an exhaustive list of historic clinical trial site data for the identified meta-data from a site data repository; (d) obtaining, via the one or more hardware processors, an exhaustive list of third party clinical trial site data for identified meta-data from a third party data repository; and (e) assessing, via the one or more hardware processors, the exhaustive list of clinical trial site data and the exhaustive list of third party clinical trial site data to obtain a list of identified clinical trial site feasibility.

In an embodiment, the plurality of protocol requirements may be structured/unstructured. In an embodiment, the meta-data may include at least one critical and relevant question identified from the received protocol requirement. In an embodiment, the meta-data may be identified based on an exhaustive list of historic meta-data present in a meta-data repository. In an embodiment, the site data repository may include data associated with at least one of (i) an exhaustive repository of historical site demographic and operational Information, (ii) a standard Key Performance Indicator (KPI), and (iii) key risk indicator (KRI). In an embodiment, the instructions when executed by the one or more hardware processors may further cause analyzing, an adequate exhaustive list of clinical trial site data. In an embodiment, the instructions when executed by the one or more hardware processors may further cause at least one of: (a) determining, at least one of: (i) clinical trial site's overall performance basis, and (ii) overall site score among initial sites from the exhaustive list of clinical trial sites by performing a trending analysis at a KPI/KRIs level across time points; and (b) estimating, a Red, Amber, and Green (RAG) score based on the overall site score. In an embodiment, the instructions when executed by the one or more hardware processors may further cause analyzing, an inadequate exhaustive list of clinical trial site data to obtain initial clinical trial site feasibility.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 4 is a user interface view illustrating a request raised to a third party data repository according to embodiments of the present disclosure.

FIG. 8 is a graphical representation illustrating a computation of a Care Performance Fraud (CPF) score for individual clinical trial site according to embodiments of the present disclosure.

DETAILED DESCRIPTION

Figure 1:
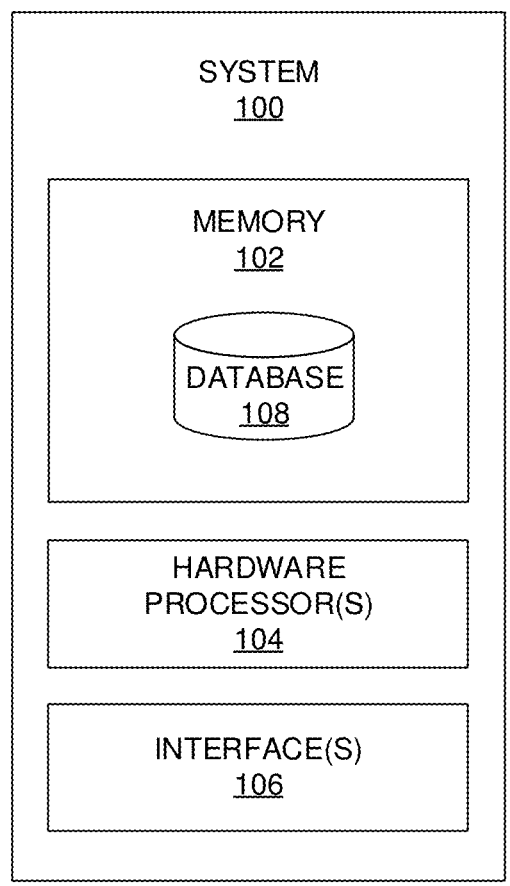
FIG. 1 illustrates a block diagram of a system to perform data driven cognitive clinical trial feasibility analysis according to embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provides a method and system for performing a data driven cognitive clinical trial feasibility analysis. In an embodiment, clinical trial feasibility is a process to evaluate possibility of conducting a clinical study in a particular region, specific medical centers/site with an objective of optimum project completion in terms of timelines, targets and cost. In an embodiment proposed system performs clinical trial site feasibility to conduct clinical trial using a data driven cognitive technique. The proposed system receives protocol requirement to initiate clinical trial site feasibility. Upon reception of protocol requirement, meta-data is identified for received protocol requirement. Further, an exhaustive list of historic and third party clinical trial site data is identified for meta-data identified for received protocol requirement. Furthermore an assessment is performed to check if exhaustive list of clinical trial site data is adequate or inadequate. Further if the exhaustive list of clinical trial site data is adequate, then an analysis is performed to obtain initial clinical trial site feasibility, else if the exhaustive list of clinical trial site data is inadequate, then missing data is estimated by a neural network module and a training module using historic data present in the system to result in initial clinical trial site feasibility.

Referring now to the drawings, and more particularly to FIG. 1 through 9, where similar reference characters denote corresponding features consistently throughout the figures, there are shown preferred embodiments and these embodiments are described in the context of the following exemplary system and/or method.

FIG. 1 illustrates a block diagram of a system 100 to perform data driven cognitive clinical trial feasibility analysis according to embodiments of the present disclosure. In an embodiment, the system 100 includes one or more processors 104, communication interface device(s) or input/output (I/O) interface(s) 106, and one or more data storage devices or memory 102 operatively coupled to the one or more processors 104. The memory 102 comprises a database 108. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

The database 108 may store information but not limited to, a plurality of parameters obtained from one or more sensors, the plurality of parameters are specific to an entity (e.g., user, machine, and the like). The database 108 includes at least one of (i) information related to clinical trial, (ii) information related to patients, and (iii) information related to clinical trial site. Further, the database 108 stores information pertaining to inputs fed to the system 100 and/or outputs generated by the system (e.g., at each stage), specific to the methodology described herein. More specifically, the database 108 stores information being processed at each step of the proposed methodology.

Figure 2:
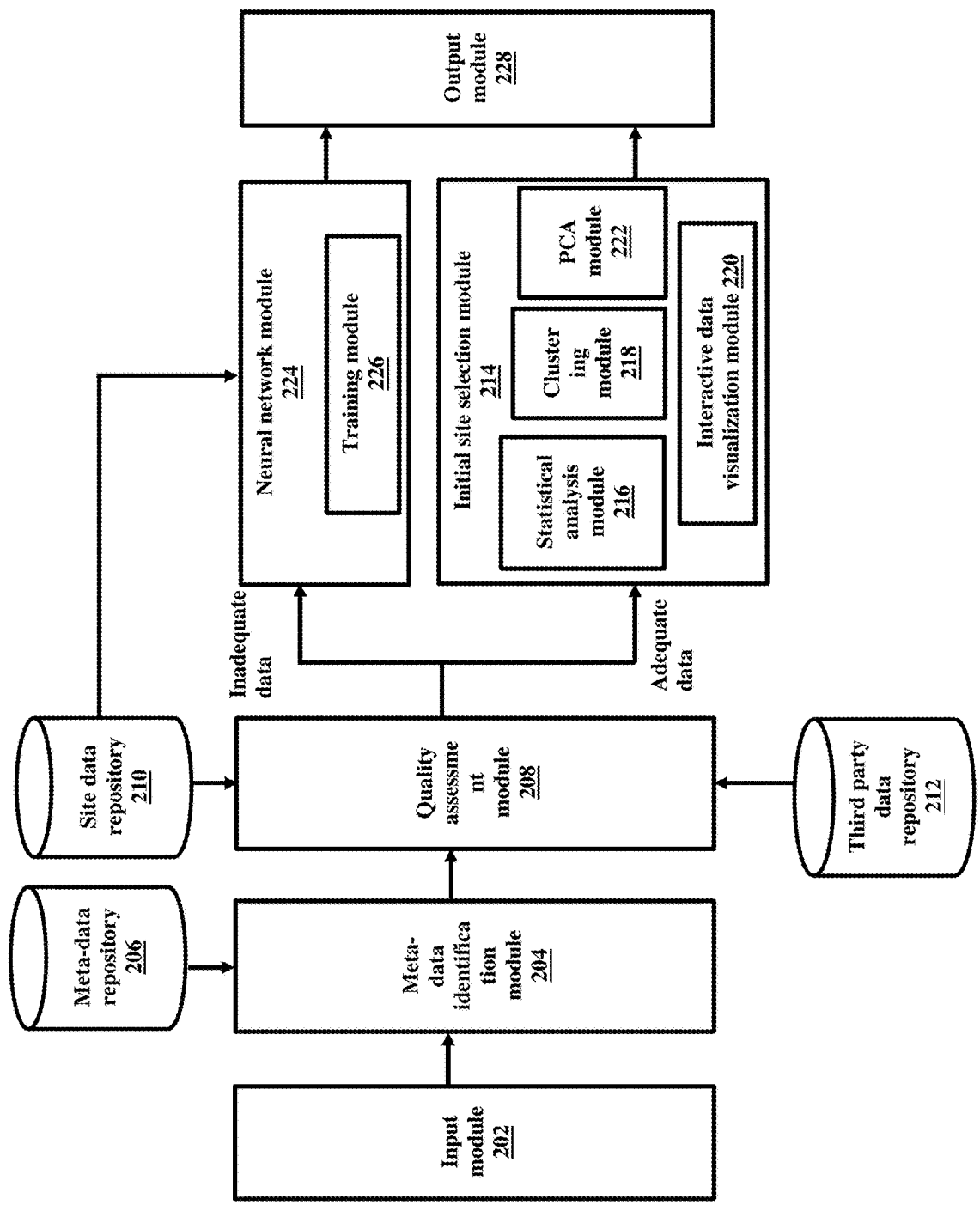
FIG. 2 illustrates a block diagram of an exemplary system to perform data driven cognitive clinical trial feasibility analysis according to embodiments of the present disclosure.

FIG. 2 illustrates a block diagram of an exemplary system 200 to perform the data driven cognitive clinical trial feasibility analysis according to embodiments of the present disclosure. The system 200 includes an input module 202, a meta-data identification module 204, a meta-data repository 206, a quality assessment module 208, a site data repository 210, a third party data repository 212, an initial site selection module 214, a neural network module 224, and output module 228. In an embodiment, the system 200 includes the input module 202 configured to receive a plurality of protocol requirements to initiate a clinical trial site feasibility analysis. In an embodiment, a meta-data is identified for received protocol requirement by the meta-data identification module 204 using the meta-data repository 206. In an embodiment, the meta-data include at least one critical and relevant question that are identified from the received protocol requirement. In an embodiment, the quality assessment module 208 is configured to identify an exhaustive list of historic and third party clinical trial site data associated with meta-data identified for received protocol requirement using the site data repository 210 and the third party data repository 212. The quality assessment module 208 is configured to perform assessment to check if exhaustive list of clinical trial site data is adequate or inadequate. In an embodiment, if the exhaustive list of clinical trial site data is adequate, then an analysis is performed by the initial site selection module 214, the initial site selection module 214 further includes a statistical analysis module 216, a clustering module 218, a Principle Component Analysis (PCA) module 222, and an interactive data visualization module 220 to obtain initial clinical trial site feasibility.

In an another embodiment, if the exhaustive list of clinical trial site data is inadequate, then missing data is estimated by the neural network module 224 and associated sub module such as a training module 226 based on a historic data present in the system to result or repository in an initial clinical trial site feasibility. In an embodiment, a list of initial clinical trial site feasibility is displayed by the output module 228. In an embodiment, the system 200 implements at least one of a logically self-contained part of a software program, a self-contained hardware component, and/or, a self-contained hardware component with a logically self-contained part of a software program embedded into each of the hardware component that when executed perform the above method described herein.

Figure 3:
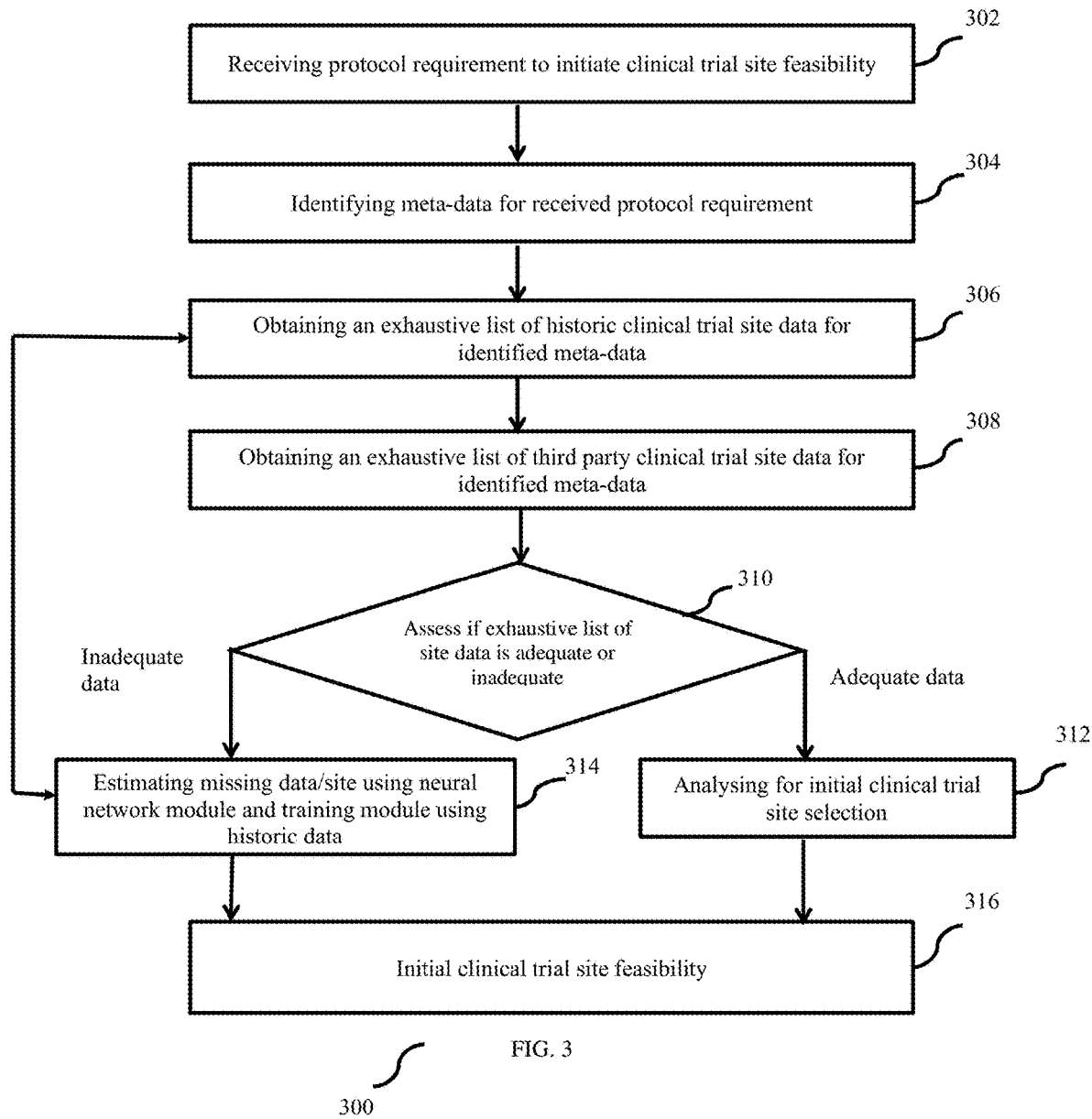
FIG. 3 is a flow diagram illustrating a method for performing the data driven cognitive clinical trial feasibility analysis according to embodiments of the present disclosure.

FIG. 3 is a flow diagram illustrating a method 300 for performing the data driven cognitive clinical trial feasibility analysis according to embodiments of the present disclosure. In an embodiment, the system 100 includes one or more data storage devices or the memory 102 operatively coupled to the one or more hardware processors 104 and is configured to store instructions for execution of steps of the method by the one or more processors 104. The flow diagram depicted is better understood by way of following explanation/description.

The steps of the method of the present disclosure will now be explained with reference to the components of the system 100 as depicted in FIG. 1. In an embodiment of the present disclosure, at step 302, the one or more hardware processors 104, a plurality of protocol requirements to initiate clinical trial site feasibility to the input module 202 is received. In an embodiment, the plurality of protocol requirements provided by one or more users may be structured or unstructured. In an embodiment, the structured plurality of protocol requirements may include at least one structured parameters such as total number of patients, Travel Allowance (TA) etc. In an embodiment, the unstructured plurality of protocol requirements may include at least one Portable Document Format (PDF) etc.

In an embodiment of the present disclosure, at step 304, the one or more hardware processors 104, a meta-data is identified for received protocol requirement in the meta-data identification module 204 using the meta-data repository 206. In an embodiment, the meta-data includes critical and relevant questions that are identified from the received protocol requirement which is used for further analysis. In an embodiment, the meta-data is identified in the meta-data identification module 204 based on an exhaustive list of historic meta-data present by the meta-data repository 206. For example, the plurality of protocol requirements and the corresponding meta-data identified is shown below in table 1:

TABLE 1

| S. NO | PROTOCOL REQUIREMENT | META-DATA IDENTIFIED |
|---|---|---|
| 1 | Principal investigator with specialty (Adolescent/Children neurology, pediatric neurology and adult neurology) | Investigator_Specialty, Age_group (Adolescent, Children, Pediatric and Adult) |
| 2 | Experience of investigator in conduct of industry sponsored clinical trials in Adolescent/pediatric population | Experience In Year, Age_group (Adolescent and Pediatric) |
| 3 | No. of patient enrolled in the past epilepsy trails | Indication (epilepsy), Sum of PatientCnt |
| 4 | Source of the patient population enrolled (e.g. hospital database, referral from other sites/physician etc.) | Patient Source (hospital database, referral from other sites/physician) |
| 5 | Adequacy of equipment for diagnosis (e.g, CT/EEG/MRI/) | Equipment Types (CT/EEG/MRI) |

In an embodiment of the present disclosure, at step 306, the one or more hardware processors 104, an exhaustive list of historic clinical trial site data is obtained for identified meta-data in the quality assessment module 208 using the site data repository 210. In an embodiment, the quality assessment module 208 obtains an exhaustive list of clinical trial site data from the site data repository 210 upon identifying the meta-data from received protocol requirement. In an embodiment, the site data repository 210 includes an exhaustive repository of historical site demographic and operational Information along with standard Key Performance Indicator (KPI) and key risk indicator (KRI), which is dynamically refreshed periodically. For example, one or more data elements present in the site data repository 210 along with an use case example of each data element is shown below in table 2:

TABLE 2

| S. NO. | DATA ELEMENT | EXAMPLE |
|---|---|---|
| 1 | Demographic | Site Location, Investigator, Country, Region . . . etc. |
| 2 | Clinical Operational Information | Current No. of Clinical Trial Ongoing, Therapeutic area, Indication, Phases . . . etc. |
| 3 | KPIs/KRIs for each data snapshot (for Trending Analysis) | Adverse Event Rate, Recruitment Rate, Discontinuation Rate, . . . etc. |

TABLE 2-continued

| S. NO. | DATA ELEMENT | EXAMPLE |
|---|---|---|
|  | as well as study level. | at each time point level. |
| 4 | Threshold/Status | RAG, Red Amber Green zone status for a particular KRI/KPIs level. |

For example, KPI's along with a description, scope and a use case example is shown below in table 3:

TABLE 3

| CATEGORY | DESCRIPTION | SCOPE | EXAMPLE |
|---|---|---|---|
| Project Milestones | Track each and every historical milestone for the study | All critical milestones dates | 1st ERB Approval-Actual |
| Patient Recruitment/Retention | These KPIs track milestones set for site to complete activities like FPFV, Recruitment, Randomization, . . . and to find how the sites have performed against those milestones | Enrolment, Recruitment, Randomization, Treatment, Discontinuation, Screen Failures | Enrollment Breakdown Basis Country |
| Data Management | These KPIs track Data Entry and Query Management. | To measure data management performance. | Query Aging Summary, Delay data Entry etc. |
| Study Compliance | These KPIs track study and the compliance (visit, dose, safety related) and patient adherence | Visit Compliance, Treatment Compliance | Patient Actual Number of Encounters (Visits) Complete |
| Safety | These KPIs track the safety aspect of drug trial | Adverse Events, ECG, Labs | Number of deaths |

In an embodiment of the present disclosure, at step 308, the one or more hardware processors 104, an exhaustive list of third party clinical trial site data is obtained for identified meta-data in the quality assessment module 208 using the third party data repository 212 as shown in FIG. 4. In an exemplary embodiment, FIG. 4 is a user interface view illustrating a request raised to a third party data repository according to embodiments of the present disclosure. In an embodiment, potential third party vendors may include Electronic Medical Record (EMR) Electronic Health Record (EHR), Third Party Structured/Unstructured data like PubMed, RSS Feeds, Practicing and Referencing App and Repository of Drug Label and Standard Medical Terminology, Medical Dictionary for Regulatory Activities (MeDRA) etc. In an embodiment, the system 200 keeps track of each request raised to the third party data repository 212.

Figure 5:
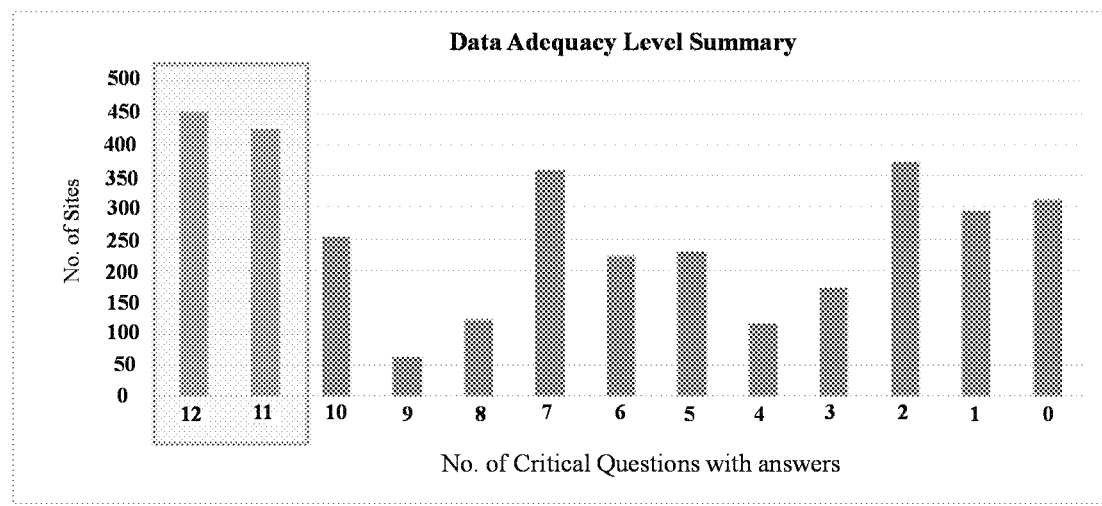
FIG. 5 is a graphical representation that depicts summary of data population of answers for plurality of critical protocol requirements according to embodiments of the present disclosure.

In an embodiment of the present disclosure, at step 310, the one or more hardware processors 104, assessment of the exhaustive list of clinical trial site data by the quality assessment module 208 to check if exhaustive list of clinical trial site data is adequate or inadequate. In an embodiment, one or more scenarios which leads to inadequacy of data, such as missing data across key critical questions, missing data within the given meta-data fields etc. For example, for missing data across key critical questions scenario, for a pediatric epilepsy clinical trial the information associated to "site experience of using computerized scoring system" is critical as related to evaluation of primary end point of protocol. Considering an example for missing data within given meta-data fields "ethic committee approval/contract finalization timeline" if "end date" meta-data value is not populated then duration of the contract finalization/ethic committee approval cannot be determined. FIG. 5 is graphical representation which depicts summary of data population of answers for plurality of critical protocol requirements and decides if data is adequate or inadequate according to example embodiments of the present disclosure.

In an embodiment of the present disclosure, at step 312, the one or more hardware processors 104, an adequate exhaustive list of clinical trial site data is analyzed by the initial site selection module 214. In an embodiment, the initial site selection module 214 further includes the statistical analysis module 216, the clustering module 218, the principal component analysis (PCA) module 222, and the interactive data visualization module 220. In an embodiment, the statistical analysis module 216, trending analysis at a KPI/KRIs level performs across time points to determine clinical trial site's overall performance basis/overall site score among initial sites from the exhaustive list of clinical trial sites. Further a Red, Amber, and Green (RAG) score is estimated based on the overall site score.

Figure 6A:
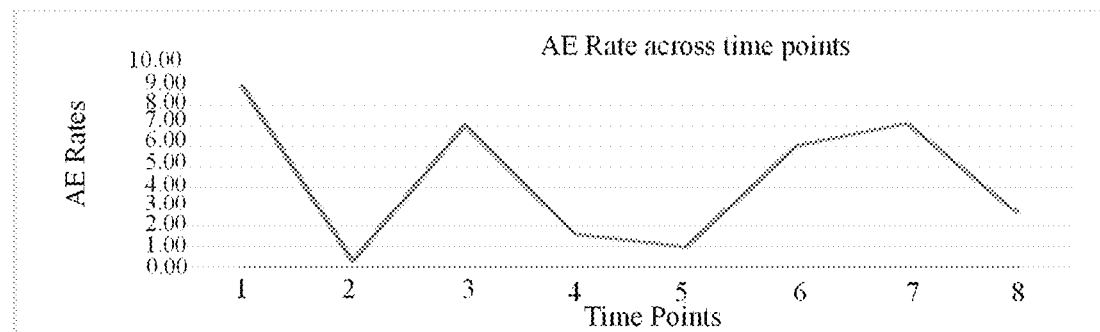
FIG. 6A and FIG. 6B is a graphical representation for a key risk indicator (KRI) level across time points and overall site score across time points correspondingly according to embodiments of the present disclosure.
Figure 6B:
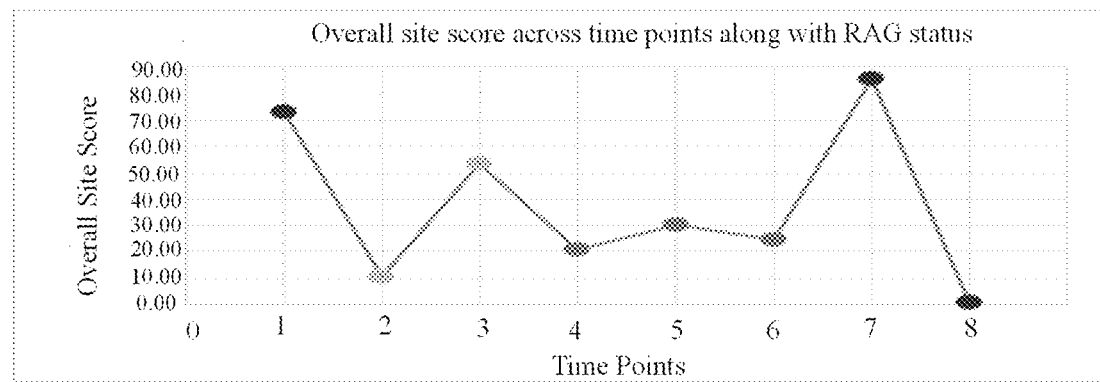

In an exemplary embodiment, FIG. 6A and FIG. 6B are a graphical representations illustrating variation of KRI level across time points and the overall site score across time points, respectively according to embodiments of the present disclosure. For example, a Mahalanobis distances (MD) technique is used to identify clinical trial sites whose KPIs/KRIs are unusual than KPIs/KRIs of other. Considering an example where clinical trial sites with a parameter Adverse Events (AE) ratio of 3.51 and the discontinuation ratio in a range of 0.24 to 1.56, however site with AE ratio in range of 1.2 to 2.2 with same range of discontinuation ratio does not comply with the usual pattern in context of other sites are selected for further analysis. For example, the MD is estimated using the expression below:

$$MD = \sqrt{a*b*c}$$

a=transpose of (data-average)
b=(inverse of variance covariance matrix) and
c=(data-average)

Figure 7:
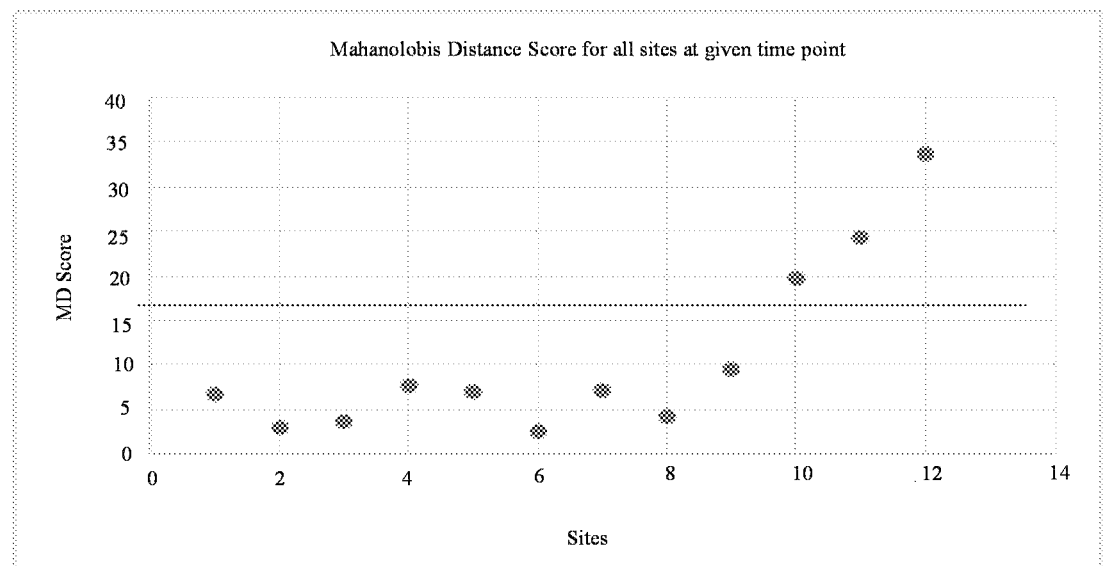
FIG. 7 is a graphical representation illustrates the Mahanolobis Distance (MD) scores for clinical trial sites at a given time point according to embodiments of the present disclosure.

FIG. 7 is a graphical representation illustrates the Mahanolobis Distance (MD) scores for clinical trial sites at a given time point according to example embodiments of the present disclosure. Further, the clinical trial site is clustered to relevant groups for auto scoring after Mahanolobis Distance (MD) analysis. In an embodiment, prior to performing auto-scoring, a Care Performance Fraud (CPF) score is computed for each clinical trial site based on at least one of following parameters: (i) Care Score: To assess the site capability of recruiting required no. of patient, (ii) Performance Score: To assess the site performance in terms of recruitment timeline, and (iii) Fraud Score: To assess those site which has fraudulence cases.

Figure 8:
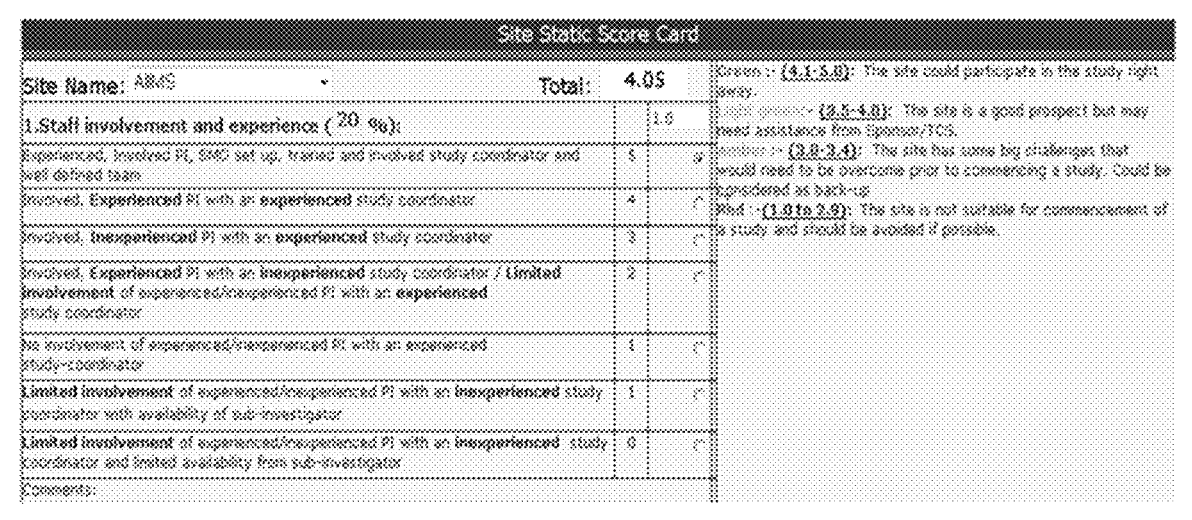

FIG. 8 is a graphical representation illustrates a computation of the Care Performance Fraud (CPF) score for individual clinical trial site according to example embodiments of the present disclosure. In an embodiment, where the CPF score is computed for each clinical trial site. Further, an automatic scoring (auto score) is estimated based on predefined scores thresholds for each zone (Red, Amber and Green) per category after computing the CPF score, which is provided as shown below in table 4:

TABLE 4

| Site | Score | Red Zone | Amber Zone | Green Zone | Zone |
|---|---|---|---|---|---|
| Potential—Care | 34 | 10-20 | 20-30 | 30-40 | Green |
| Reliable—Forgery | 43 | 30-40 | 40-50 | 50-60 | Amber |

TABLE 4-continued

| Site | Score | Red Zone | Amber Zone | Green Zone | Zone |
|---|---|---|---|---|---|
| Selectable—Performance | 45.5 | 30-40 | 40-50 | 50-60 | Amber |

Figure 9:
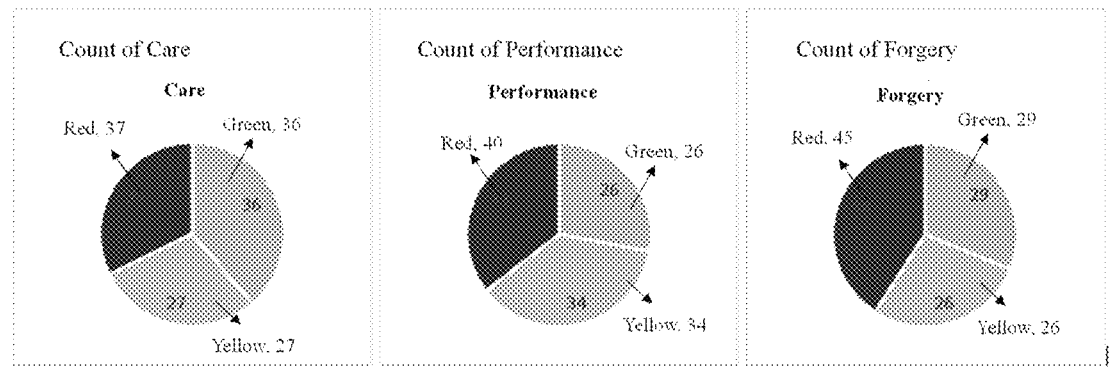
FIG. 9 is a graphical representation illustrating an interactive data visualization of the clinical trial sites falling under three zones for each category displayed for initial site selection according to embodiments of the present disclosure.

In an exemplary embodiment, based on the auto scoring and above configuration, in the interactive data visualization module 220, an interactive data visualization of the clinical trial sites falling under all the three zones (Red, Amber, and Green) for each category (Care, Performance and Forgery) is displayed for initial site selection as shown in FIG. 9. In an embodiment, principle component analysis (PCA) along with Eigen value determination is performed by the PCA module 222 to obtain PCA score. Furthermore, based on the PCA score, the clinical trial sites are ranked and tiered to identify initial list of clinical trial sites to be displayed by the output module 228.

In an embodiment of the present disclosure, at step 314, the one or more hardware processors 104, the inadequate exhaustive list of clinical trial site data is analyzed by the neural network module 224 and the training module 226. In an embodiment, the inadequate exhaustive list of clinical trial site data is processed by the neural network module 224 and the training module 226 to obtain initial clinical trial site feasibility. The inadequate clinical data shared with the neural network module 224 and the training module 226 is cleaned up and formatted before being used to estimate missing data. Since clinical trial site data is inadequate, the missing data is estimated using the neural network module 224 and the training module 226. In an embodiment, the training module 226 is a machine learning system that uses historic data present in the site data repository 210 to train itself and aid the neural network module 224 to estimate missing data and also to identify initial list of clinical trial sites to be displayed in the output module 228. In an embodiment of the present disclosure, at step 316, the one or more hardware processors 104, a list of identified initial clinical trial site feasibility is displayed by an output module 228.

The embodiments of the present disclosure brings an objective, transparent, evidence based and logical method of feasibility assessment for site selection, which utilizes multiple level information from various sources including public data and social media in feasibility assessment exercise. The embodiments of the present disclosure brings an independent method which does not require to depend upon feasibility questionnaire or any subjective information for feasibility determination. The embodiments of the present disclosure which utilizes known and tested surveillance methods that provide not only the site's credentials in terms of training and facility, but also in terms of the capabilities for care, medical management, availability of the relevant subjects pool etc. The embodiments of the present disclosure in which disruption of the site feasibility and selection methods by going top-down by fetching higher number of sites and providing a wider and transparent choice based upon a critical scores. Thus the embodiments herein provide a method and a system for data driven cognitive clinical trial feasibility program which also includes clinical trial site feasibility to conduct clinical trial.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for performing a data driven cognitive clinical trial feasibility analysis, comprising:
    receiving, via one or more hardware processors, a plurality of protocol requirements to initiate a clinical trial site feasibility;
    identifying, via the one or more hardware processors, a plurality of meta-data for at least one protocol requirement from the plurality of protocol requirements, wherein the plurality of meta-data include details of specialty of an investigator including experience of the investigator in year in conducting clinical trials, experience in year related to therapeutic area and the indication, number of patients investigated, source of patients enrolled from a hospital database, referral from website, medical equipment types in a clinical trial site corresponding to the protocol requirement;
    obtaining, via the one or more hardware processors, a list of historic clinical trial site data for the identified meta-data from a site data repository (210);
    obtaining, via the one or more hardware processors, a list of third party clinical trial site data for identified meta-data from a third party data repository (212) and maintaining a track of each request raised to the third party data repository (212), wherein the request is raised to the third party data repository (212) through an user interface;
    assessing, via the one or more hardware processors, the list of clinical trial site data and the list of third party clinical trial site data to obtain a list of identified clinical trial site feasibility;
    analyzing, via the one or more hardware processors, the list of clinical trial site data by a machine learning system (226) to self-train with the list of historic clinical trial site data present in the site data repository (210); and
    estimating missing data corresponding to the meta-data from the historic clinical trial site data present in the site data repository (210) including a demographic information of the clinical trial site and the investigator, an operational information of the clinical trial site including a number of ongoing clinical trials, therapeutic area, a Key Performance Indicator (KPI) including an enrollment rate, a screen failure rate, adverse event rate, a recruitment rate, a discontinuation rate, and a key risk indicator (KRI), a status of the historic clinical trial site, to identify an initial list of clinical trial sites to display in the user interface, by a neural network module (224); and
    computing a care performance fraud (CPF) score for each clinical trial site based on a care score to assess site capability of recruiting required number of patients, a performance score to assess site performance in terms of a recruitment timeline, and a fraud score to assess clinical trial site with fraudulent cases.

2. The processor implemented method of claim 1, wherein the plurality of protocol requirements are one of structured or unstructured.

3. The processor implemented method of claim 1, wherein the meta-data comprises at least one question identified from the received protocol requirement, wherein the meta-data is identified based on a list of historic meta-data present in a meta-data repository (206).

4. The processor implemented method of claim 1, the demographic information and the operational information, the KPI and the KRI are dynamically refreshed in the site data repository periodically.

5. The processor implemented method of claim 1, further comprising, at least one of:
(a) determining, by via the one or more hardware processors, at least one of: (i) clinical trial site's overall performance basis, and (ii) overall site score among initial sites from the list of clinical trial sites by performing a trending analysis at a KPI/KRIs level across time points to compare KPI/KRIs level of one clinical trial site with KPI/KRIs level of another clinical trial site, wherein the clinical trial site with a range of ratio of adverse event is within same range of ratio of the discontinuation is considered for the trending analysis; and
(b) estimating, status as a Red, Amber, and Green (RAG) score based on the overall site score.

6. A system (100) to perform a data driven cognitive clinical trial feasibility analysis, wherein the system comprising:
a memory (102) storing instructions;
one or more communication interfaces (106); and
one or more hardware processors (104) coupled to the memory (102) via the one or more communication interfaces (106), wherein the one or more hardware processors (104) are configured by the instructions to:
receive, a plurality of protocol requirements to initiate a clinical trial site feasibility;
identify, a plurality of meta-data for at least one protocol requirement from the plurality of protocol requirements, wherein the plurality of meta-data include details of specialty of an investigator including experience of the investigator in year in conducting clinical trials, experience in year related to therapeutic area and the indication, number of patients investigated, source of patients enrolled from a hospital database, referral from website, medical equipment types in a clinical trial site corresponding to the protocol requirement;
obtain, a list of historic clinical trial site data for the identified meta-data from a site data repository (210);
obtain, a list of third party clinical trial site data for identified meta-data from a third party data repository (212) and maintain a track of each request raised to the third party data repository (212), wherein the request is raised to the third party data repository (212) through an user interface;
assess, the list of clinical trial site data and the exhaustive list of third party clinical trial site data to obtain a list of identified clinical trial site feasibility;
analyzing the list of clinical trial site data by a machine learning system (226) to self-train with the list of historic clinical trial site data present in the site data repository (210); and
estimating missing data corresponding to the meta-data from the historic clinical trial site data present in the site data repository (210) including a demographic information of the clinical trial site and the investigator, an operational information of the clinical trial site including a number of ongoing clinical trials, therapeutic area, a standard Key Performance Indicator (KPI) including an adverse event rate, a recruitment rate, a discontinuation rate, and a key risk indicator (KRI), a status of the historic clinical trial site, to identify an initial list of clinical trial sites to display in the user interface, by a neural network module (224); and
computing a care performance fraud (CPF) score for each clinical trial site based on a care score to assess site capability of recruiting required number of patients, a performance score to assess site performance in terms of a recruitment timeline, and a fraud score to assess clinical trial site with fraudulent cases.

7. The system of claim 6, wherein the plurality of protocol requirements are one of structured or unstructured.

8. The system of claim 6, wherein the meta-data comprises at least one question identified from the received protocol requirement, wherein the meta-data is identified based on a list of historic meta-data present in a meta-data repository (206).

9. The system of claim 6, the demographic information and the operational information, the KPI and the KRI are dynamically refreshed in the site data repository periodically.

10. The system of claim 6, the one or more hardware processors are further configured to, at least one of:
(a) determine, by via the one or more hardware processors, at least one of: (i) clinical trial site's overall performance basis, and (ii) overall site score among initial sites from the list of clinical trial sites by performing a trending analysis at a KPI/KRIs level across time points to compare KPI/KRIs level of one clinical trial site with KPI/KRIs level of another clinical trial site, wherein the clinical trial site with a range of ratio of adverse event is within same range of ratio of the discontinuation is considered for the trending analysis; and
(b) estimate, status as a Red, Amber, and Green (RAG) score based on the overall site score.

* * * * *